United States Patent [19]

Chamness

[11] 4,294,254
[45] Oct. 13, 1981

[54] SURGICAL APPARATUS

[76] Inventor: Dale L. Chamness, 621 Pleasant Ridge Rd., Bloomington, Ind. 47401

[21] Appl. No.: 86,588

[22] Filed: Oct. 19, 1979

Related U.S. Application Data

[63] Continuation-in-part of Ser. No. 858,712, Dec. 8, 1977, Pat. No. 4,256,113.

[51] Int. Cl.³ .......................................... A61B 17/00
[52] U.S. Cl. ............................................... 128/303.14
[58] Field of Search .................. 128/303.15, 303.14, 128/303.16, 303.17, 328, 307, 309

[56] References Cited

U.S. PATENT DOCUMENTS

| | | | |
|---|---|---|---|
| 3,149,633 | 9/1964 | Zingale | 128/303.15 |
| 3,811,446 | 5/1974 | Lerwick et al. | 128/328 |
| 3,955,578 | 5/1976 | Chamness et al. | 128/303.15 |

FOREIGN PATENT DOCUMENTS

| | | | |
|---|---|---|---|
| 2131974 | 6/1977 | Fed. Rep. of Germany | 128/236 |
| 427719 | 2/1975 | U.S.S.R. | 128/236 |

*Primary Examiner*—John D. Yasko
*Attorney, Agent, or Firm*—Jenkins, Coffey, Hyland, Badger & Conard

[57] ABSTRACT

A surgical cannula includes a sheath having proximal and distal ends, a member disposed within the sheath and movable longitudinally therein, the movable member having proximal and distal ends, and a surgical instrument operable by movement of the distal end of the movable member with respect to the distal end of the sheath. The cannula further includes an operating assembly comprising a body or handle which slidably receives a slide for movement longitudinally of the body. The body defines a generally cylindrical interior and the slide includes a pair of longitudinally spaced-apart walls having the same general shape as the cross section of the cylinder. The walls are provided with aligned apertures which rotatably receive a stem. The stem includes proximal and distal ends, and the proximal end of the movable member is fixedly attached to the distal end of the stem. The proximal end of the sheath is fixedly attached to the body portion of the handle. The stem is provided with a thumbwheel which is accessible through the side wall of the body, the thumbwheel being manipulatable to rotate the movable member in the sheath. The slide includes a rack, and the body supports an additional thumbwheel having pinion gear teeth formed thereon, the pinion gear teeth engaging the rack. Manipulation of the second-mentioned thumbwheel causes the slide to move longitudinally within the body to move the movable member longitudinally within the sheath.

14 Claims, 13 Drawing Figures

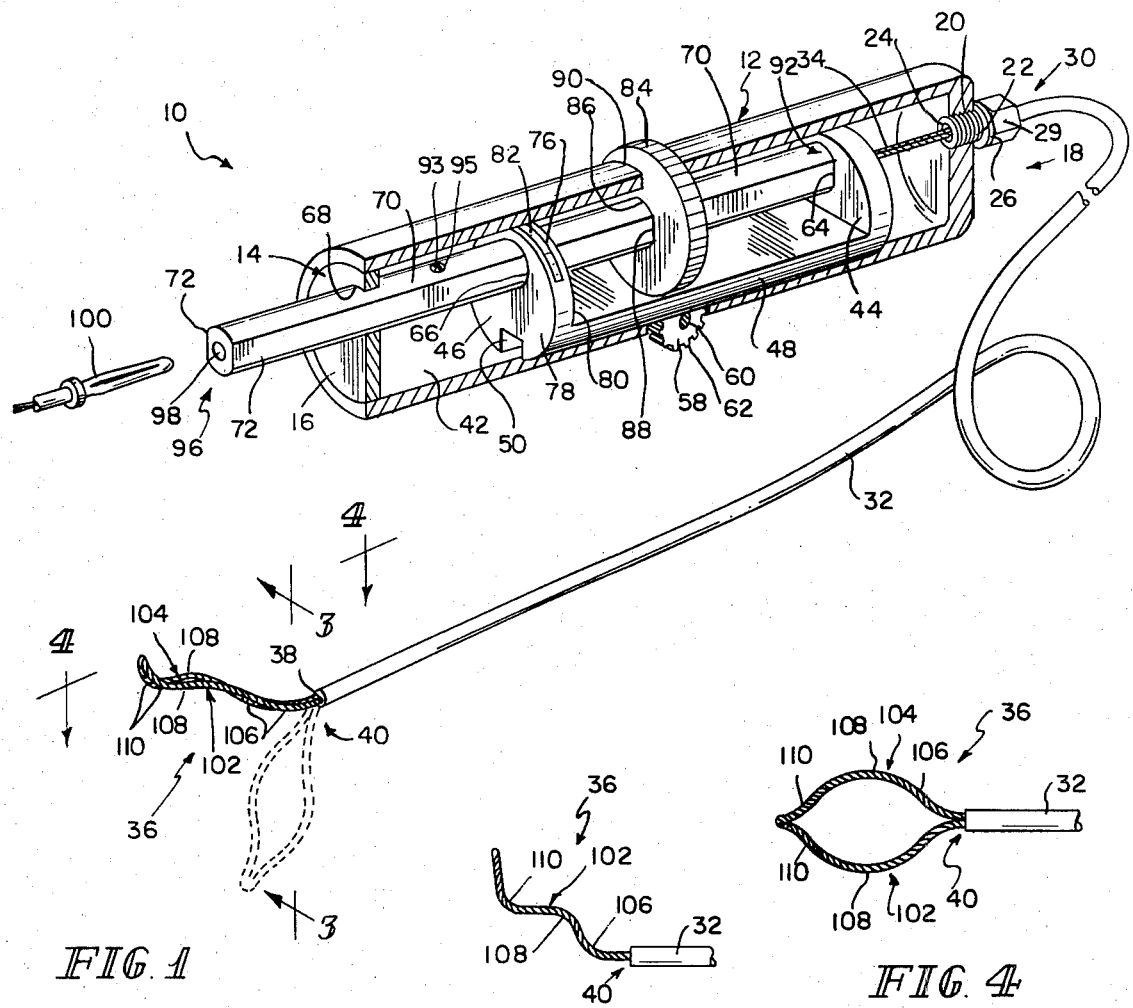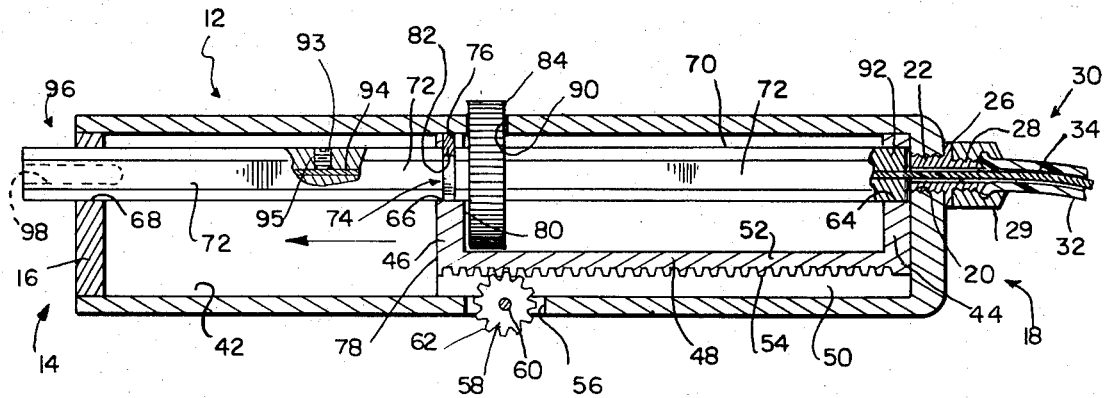

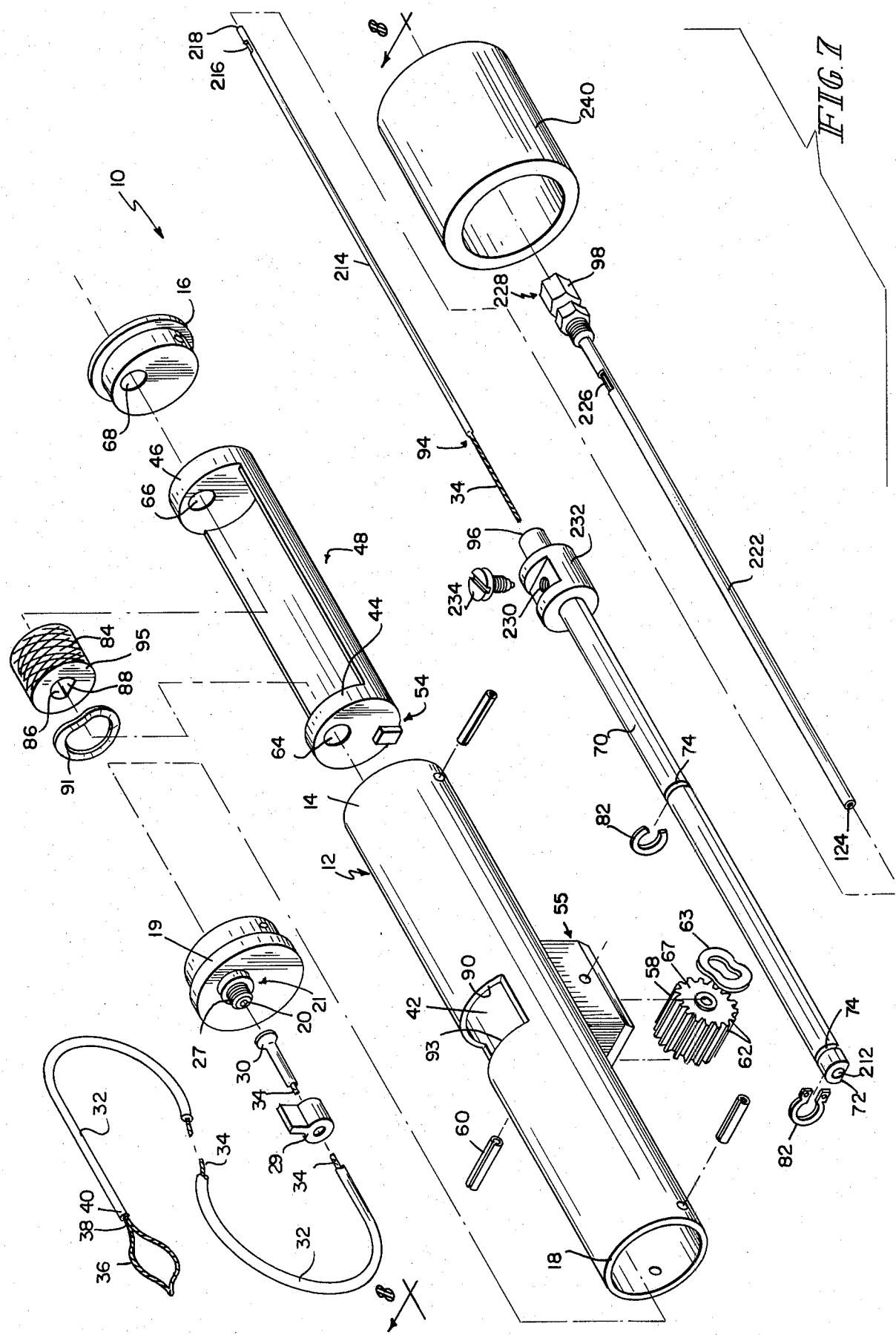

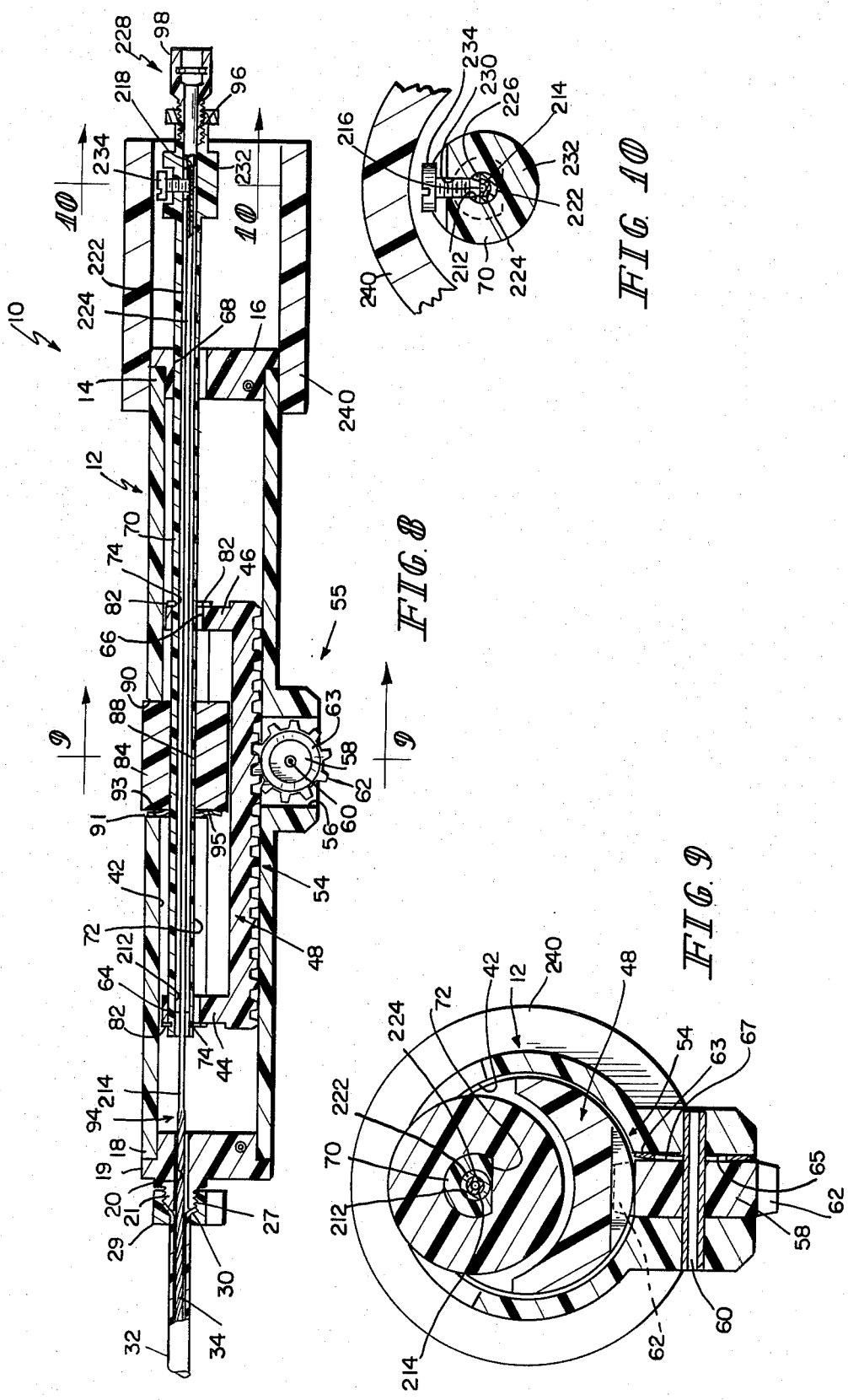

SURGICAL APPARATUS

This is a continuation-in-part of prior co-pending application Ser. No. 858,712, filed Dec. 8, 1977, now U.S. Pat. No. 4,256,113.

This invention relates to surgical instruments generally, and more particularly to a surgical snare manipulating apparatus useful for operating polypectomy apparatus, polyp and foreign body retrieval apparatus, cytology brush apparatus, and similar apparatus.

Surgical snares suitable for use in removing polyps, such as those found in the gastrointestinal tract, have been in use for many years. A surgical snare generally includes an elongated flexible sheath connected at its proximal end to an operating handle. Extending through the sheath is an elongated flexible cable, the proximal end portion of which is connected to a movable portion of the operating handle so that the cable can be retracted and protracted by the surgeon relative to the sheath. An operating loop is connected to the distal end portion of the cable which is opened and closed by the surgeon to the extent that he shifts the movable portion of the operating handle to protract or retract the cable. When the cable is in its protracted or forward position, the operating loop is outside the sheath and in its fully extended position. As the cable is retracted, the loop is drawn into the sheath and closed.

Prior art surgical snares have generally suffered from common deficiencies such as ease of manipulation of the operating loop at the point of application, for example, within the gastrointestinal tract of a surgical patient. As can be appreciated, during periods of use, a surgical snare must be manipulated and operated with considerable precision and control.

In addition, many prior art snare handles for use with the available surgical snares are designed so that in order to engage the polyp, it is necessary to rotate the entire handle in order to rotate the operating loop. The operating loop handle usually is connected by an electrical conductor to an RF generator. The conductor has a tendency to become wrapped around the surgeon's hand as he rotates the handle to engage the polyp. Other prior art snares require two-handed operation to rotate and protract or retract the snare simultaneously. This is disadvantageous in that the surgeon may be trying to operate one or more other instruments at the same time he is operating the snare. Prior art structures are found in Chamness et al U.S. Pat. No. 3,955,578 and references cited therein.

Other structures are found in the following: U.S. Pat. No. 1,971,024; U.S. Pat. No. 2,448,741; U.S. Pat. No. 2,484,059; U.S. Pat. No. 3,552,384; U.S. Pat. No. 3,955,578; Swiss Patent Publication No. 192,928; German Patent Specification No. 1,250,052; U.S. Pat. No. 3,081,767; and U.S. Pat. No. 3,149,633.

According to the present invention, an apparatus is provided for use with a polypectomy instrument, polyp or foreign body retrieval instrument, cytology brush instrument, or other similar instruments. The apparatus includes a sheath having proximal and distal ends, and a member disposed within the sheath and movable longitudinally therein, the movable member having proximal and distal ends, and a surgical instrument operable by movement of the distal end of the movable member with respect to the distal end of the sheath. The inventive apparatus, an operating assembly for the instrument, comprises first means for moving the movable member longitudinally with respect to the sheath, second means for rotating the movable member within the sheath, and a body for supporting the first and second means, the body including a distal end for fixed attachment of the proximal end of the sheath thereto, the distal end of the body further defining an aperture through which the proximal end of the movable member extends, the proximal end of the movable member being coupled to the first and second means for movement thereby.

In an illustrative embodiment, the first means includes a slide supported in the body for movement longitudinally thereof, the body including means defining a generally cylindrical interior wall and the slide including means providing a pair of walls spaced apart longitudinally of the cylinder axis and shaped to slide in the cylinder, the walls having substantially the same shape as a cross section of the body interior wall. The slide further comprises a portion defining a rack and the body includes a first thumbwheel, the periphery of which provides pinion gear teeth to engage the rack. Manipulation of the first thumbwheel causes movement of the slide longitudinally within the body, and corresponding protraction and retraction of the distal end of the movable member with respect to the distal end of the sheath to operate the surgical instrument.

Further according to the illustrative embodiment, the second means comprises a stem rotatably mounted with respect to the first means by being received in aligned apertures in the longitudinally spaced-apart walls of the slide. The stem has proximal and distal ends, the proximal end of the movable member being fixedly attached to the distal end of the stem. The stem includes a second thumbwheel for manipulation to rotate the stem with respect to the first means, the second thumbwheel being accessible through the body. The proximal end of the stem includes means defining a terminal for attachment to a source of electrical energy and a conductor providing electrical contact between the terminal and the proximal end of the movable member. The movable member includes electrically conductive means to supply electricity to the surgical instrument.

Further according to the instant invention, a surgical cannula includes a sheath and a snare extending within the sheath and having proximal and distal ends, a loop formed at the distal end of the snare, and means for protracting the distal end of the snare including the loop from, and retracting the distal end of the snare including the loop into, the distal end of the sheath, the loop being formed with a double offset bend in a plane extending longitudinally of the cannula across the loop, such that partial retraction of the loop into the distal end of the sheath causes the loop to move parallel to the first-mentioned plane and perpendicular to a second plane which is perpendicular to the first-mentioned plane and parallel to the longitudinal extent of the cannula. In the illustrative embodiment, the loop is somewhat W-shaped in the first-mentioned plane, such that partial retraction of the loop into the sheath causes the portion of the loop remote from the sheath to move parallel to the first-mentioned plane and perpendicular to the second-mentioned plane.

Further according to illustrative embodiments of the invention, a surgical apparatus includes a body providing an interior, a slide slidable within the interior, a stem rotatably mounted on the slide, first means for controlling movement of the slide within the handle, and second means for controlling rotation of the stem with respect to the slide. The body includes first and second openings. An elongated sheath movably supports a snare wire. The snare wire is electrically conductive. The proximal end of the sheath is attached to the body and the proximal end of the snare wire extends through the first opening. A snare is provided on the distal end of the snare wire for protraction, retraction and rotation with respect to the distal end of the sheath in response to movement of the slide and stem. The stem is provided with a longitudinally extending first passageway. The stem first passageway receives a conductive tip on the proximal end of the snare wire from the stem distal end, and a conductive sleeve for insertion through the second opening in the body into the stem first passageway to engage the tip in conductive engagement. Electrical power is supplied through this connection to the snare.

In illustrative embodiments of the invention, the sleeve includes an opening having an inside dimension substantially equal to an outside dimension of the tip to engage the tip slidably to provide the conductive engagement. The stem further includes a second passageway intersecting the first passageway. The sleeve includes an opening for alignment with the second passageway when the sleeve is inserted fully into the stem first passageway. The tip includes a notch for alignment with the stem second passageway and sleeve opening. A pin is inserted into the stem second passageway, through the sleeve opening and into the tip notch to fix the sleeve and tip against shifting movement longitudinally of the stem first passageway. The pin and stem second passageway are threaded to prevent unintentional movement of the pin out of engagement with the stem, sleeve and tip.

The invention may best be understood by referring to the following description and accompanying drawings which illustrate the invention. In the drawings:

FIG. 1 is a partly sectional fragmentary isometric view of an apparatus constructed according to the present invention;

FIG. 2 is a vertical sectional side elevational view of a portion of the apparatus of FIG. 1;

FIG. 3 is a fragmentary sectional view of the surgical snare loop of the apparatus of FIG. 1, taken generally along section lines 3—3 thereof;

FIG. 4 is a fragmentary sectional view of the surgical snare loop of the apparatus of FIG. 1, taken generally along section lines 4—4 thereof;

FIG. 7 is an exploded perspective view of another apparatus constructed according to the present invention;

FIG. 8 is a sectional side elevational view of the apparatus of FIG. 7, taken generally along section lines 8—8 thereof;

FIG. 9 is a sectional view of a detail of the apparatus of FIGS. 7-8, taken generally along section lines 9—9 of FIG. 8;

FIG. 10 is a fragmentary sectional view of a detail of the apparatus of FIGS. 7-9 taken generally along section lines 10—10 of FIG. 8;

Figure 5:
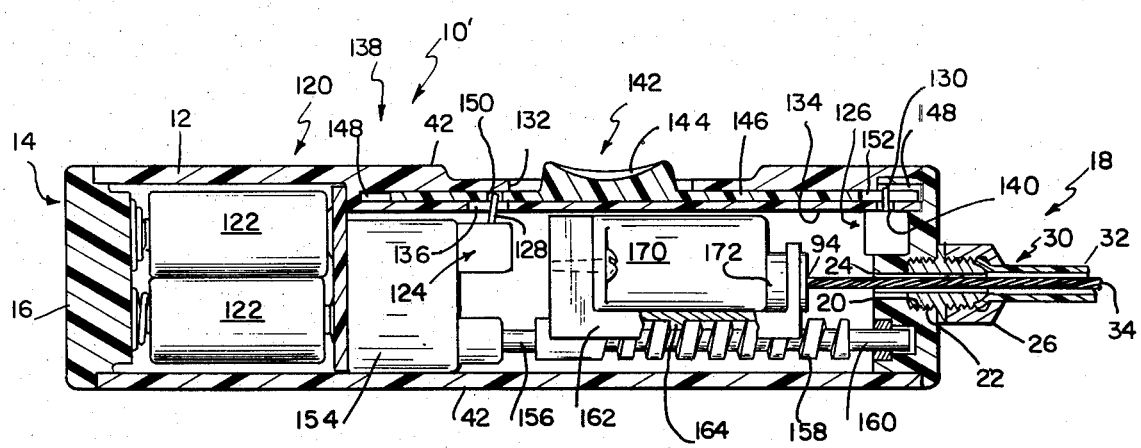
FIG. 5 is a sectional side elevational view of another apparatus constructed according to the present invention.

The apparatus 10 of the instant invention includes a cannula operating handle or body 12 having a proximal end 14, covered by an end cap 16 and a distal end 18. Distal end 18 includes a threaded aperture 20 which receives a nut 22, also having an aperture 24 extending longitudinally therethrough. Nut 22 is provided with a collar 26 and a forwardly extending portion 28 having outside threads for threadedly engaging a nut 29 (FIG. 2).

The flared proximal end 30 of a cannula sheath 32 is urged onto portion 28 and held in place by tightening nut 29 on threaded portion 28. Sheath 32 is hollow and receives a movable member or snare wire 34, the diameter of snare wire 34 being sufficiently small that it is freely slidable longitudinally of sheath 32. A snare loop 36 is formed at the distal end 38 of snare wire 34, loop 36 extending beyond the distal end 40 of sheath 32. The particular structure of snare loop 36 in the illustrated embodiment will be discussed subsequently.

The cannula operating handle or body 12 includes a generally right circular cylindrical inner wall 42 which slidingly engages the forward and rearward end walls 44, 46, respectively, of a slide 48. As best illustrated in FIG. 1, the walls 44, 46 are generally circular to the shape to conform to the cross section of inner wall 42 transversely of the longitudinal extent of handle or body 12. Slide 48 further includes a longitudinally extending channel 50 opening downwardly and provided at its vertically upper extent 52 with a plurality of teeth forming a rack 54. Rack 54 extends substantially the full length of slide 48 in the channel 50.

Body 12 is provided with a slot 56 (FIG. 2) through the side wall thereof. A first thumbwheel 58 is mounted upon an axle 60 for rotation in slot 56. The periphery of thumbwheel 58 is provided with a plurality of teeth 62 to form a pinion gear which engages rack 54. Manipulation of thumbwheel 58 causes slide 48 to slide longitudinally within body 12.

Forward and rearward end walls 44, 46 are provided with circular cross section aligned apertures 64, 66, respectively. An aperture 68, which is in alignment with apertures 64, 66, is provided in end cap 16. All of apertures 64, 66, 68 are also generally in alignment with aperture 24 in nut 22. A stem 70, which is generally circular in cross section and provided with diametrically opposed, longitudinally extending flats 72, is received in apertures 64, 66, 68. Stem 70 is provided with a reduced diameter circular cross section portion 74. Rearward wall 46 of slide 48 is provided with a slot 76 in the vertically upper portion thereof, the slot 76 extending generally parallel to the axially facing surfaces 78, 80 of wall 46. A somewhat C-shaped keeper 82 is positioned in slot 76, the keeper engaging the reduced diameter portion 74 of stem 70 to position stem 70 longitudinally with respect to slide 48, while at the same time permitting rotation of stem 70 about its axis within apertures 64, 66. A second thumbwheel 84 having a generally circular aperture 86 (FIG. 1) with flats 88 on both sides thereof is longitudinally slidably mounted on stem 70. Flats 88 engage flats 72 on the stem, such that rotation of thumbwheel 84 causes rotation of stem 70. Thumbwheel 84 is positioned between walls 44, 46 and is accessible through a peripherally extending slot 90 in the wall 42 of body 12 for manipulation to rotate stem 70.

The distal end 92 of stem 70 receives the proximal end 94 of snare wire 34. Proximal end 94 of snare wire 34 extends through stem 70 to near the proximal end 96 thereof. Proximal end 94 of snare wire 34 is held in place in stem 70 by a set screw 93 which is inserted through a threaded bore 95 in the stem 70 side wall. Movement of the stem 70 is transmitted to snare wire 34, and through snare wire 34 to the snare loop 36. Typically, snare wire 34 and loop 36 will be constructed from electrically conductive materials, with the sheath 32 constructed from an insulative material. Generally, of course, wire 34 and sheath 32 are fairly flexible to pass with little difficulty and without resulting injury through, for example, the gastrointestinal tract of a person upon whom a polypectomy procedure is to be performed. The proximal end 96 of stem 70 is provided with a terminal or socket 98 adapted to receive a male plug 100 (FIG. 1) of an RF generator (not shown). Radio frequency energy supplied from the generator through plug 100, socket 98, and intermediate conductor (not shown) which extends longitudinally within stem 70, and snare wire 34 to loop 36, is used to cauterize the area resulting from removal of a polyp or other obstruction which is removed from, for example, the gastrointestinal tract.

The polypectomy apparatus 10 structure thus far described provides significant advantages over such prior art structures as, for example, the structure of U.S. Pat. No. 3,955,578 in that the snare-operating handle construction permits one-handed operation of the polypectomy apparatus, both for snare protraction and retraction and for snare rotation, by a surgeon. This is important as well as convenient for the surgeon since, in a typical application, the surgeon will be operating a light source for illuminating the surgery site, observing the surgical procedure, e.g., by means of an optical waveguide, and operating a polyp retriever, concurrently with the operation of the snare.

Attention is now drawn to the configuration of the snare loop 36 itself. It may be seen that, unlike known prior art loops, snare loop 36 is not generally flat and planar. Rather, each side of snare loop 36 is bent, as best illustrated in FIG. 3, into a somewhat W-shaped configuration. Generally, each side 102, 104 of loop 36 is bent at 106, 108, 110 into this "double-bent" configuration.

As can be seen from FIG. 3, a view taken generally in a first plane which extends longitudinally of the cannula across the loop 36, and FIG. 4, a view taken generally in a plane which is perpendicular to the first plane and parallel to the longitudinal extent of the cannula, partial retraction of the loop 36 into the distal end 40 of sheath 32 (such partial retraction being across the bend 106 but not across the bend 108 in each of sides 102, 104 of loop 36) causes the loop 36 to move parallel to the first plane and perpendicular to the second plane in somewhat of a "flipping" motion. This flipping of the loop 36 within, for example, the intestine of a surgical patient can be used to advantage by the surgeon-operating apparatus 10 to ensnare a polyp for removal. The position of loop 36 after flipping is illustrated in broken lines in FIG. 1. This feature aids substantially the utility of the loop 36.

Figure 6:
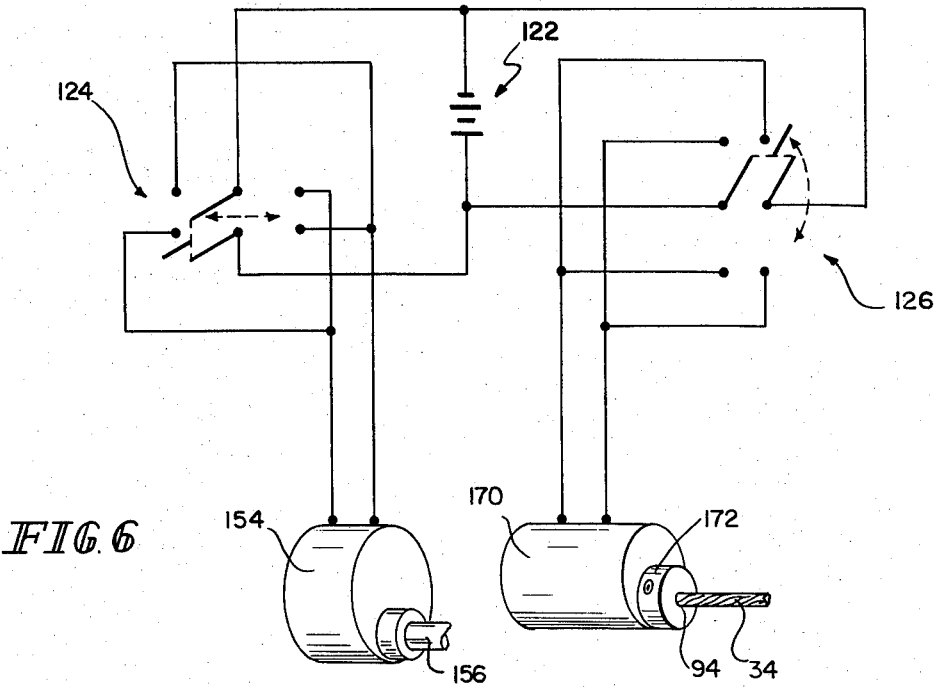
FIG. 6 is a partly block and partly schematic diagram showing the wiring of the electrical system of the embodiment of FIGS. 5-6.

Turning now to the embodiment of the invention illustrated in FIGS. 5-6, those elements numbered identically with the elements in the embodiments of FIGS. 1-2 perform the same or similar functions. The apparatus 10' of FIG. 5 includes the cannula operating handle or body 12 having a proximal end 14 covered by end cap 16 and a distal end 18. The proximal end 30 of the cannula sheath 32 is attached to the distal end 18 in the same manner as in the embodiment of FIGS. 1-2, i.e., through a threaded aperture 20, a nut 22 having an aperture 24, and a collar 26.

The cannula operating handle 12 includes an inner proximal or rearward end portion 120 housing a suitable power source, in this embodiment, a pair of dry cells 122. Dry cells 122 are coupled through suitable electrical conductors to a double-pole, double-throw, protract/retract electrical switch 124, and a similar double-pole double-throw, rotate right/rotate left switch 126. Each of switches 124, 126 includes an operating lever 128, 130, respectively. Switches 124, 126 are housed within the generally right circular cylindrical body 12 adjacent a thumb control opening 132 through the cylindrical wall 42 of body 12. Body 12 is further provided with an interior generally cylindrical wall 134 which extends part way around the inner periphery of body 12 and includes a longitudinally extending slot 136 adjacent the rearward or proximal end 138 of thumb control opening 132, and a peripherally extending slot 140 adjacent the forward or distal end 18 of body 12. A thumb control 142 having a thumb-engaging portion 144 projecting above the cylindrical side wall of body 12, and a part-cylindrical portion or skirt 146 is mounted in the body 12. The thumb-engaging portion 144 projects through the thumb-control opening 132 for access by an operator, and the skirt 146 is freely slidably received within the space 148 defined between outer cylindrical wall 42 and the inner part-cylindrical wall 134. The skirt 146 of control 142 includes a peripherally extending slot 150 which receives the operating lever 128 of the protract/retract switch 124, and a longitudinally extending slot 152 which receives the operating lever 130 of the rotate right/rotate left switch 126.

Switch 124 is coupled by suitable electrical conductors to the terminals of a protract/retract motor-transmission 154 which includes a reversible DC motor. The output shaft 156 of motor-transmission 154 is coupled to a worm 158 which is suitably journalled for rotation at its forward end 160 within body 12. A carrier 162 is mounted upon worm 158, the carrier 162 including a follower 164 which advances the entire carrier 162 toward the distal end of body 12 as the worm 158 is rotated in one direction and retracts the carrier 162 from the distal end of body 12 as worm 158 is rotated in the opposite direction, the carrier 162 being slidably mounted within the generally cylindrical side wall 42 of body 12.

Rotate right/rotate left switch 126 is coupled through suitable conductors to a rotate right/rotate left motor-transmission 170 which is mounted upon carrier 162 for movement therewith. The conductors coupling motor-transmission 170 to switch 126 permit such movement of the motor-transmission 170. The proximal end 94 of snare wire 34 is coupled directly to the output shaft 172 of the rotate right/rotate left motor-transmission 170.

In operation, the thumb control 142 of the embodiment of FIGS. 5-6 is permitted to slide forwardly and rearwardly longitudinally of housing 12 without damaging operating lever 130 by the longitudinally extending slot 152 in skirt 146. The engagement of operating lever 128 in the peripherally extending slot 150 of skirt 146 causes actuation of the protract/retract switch 124 and motor-transmission 154 to protract the snare 36 from the distal end 38 of sheath 32. Movement of thumb control 142 longitudinally rearwardly (toward the proximal end) of body 12 actuates the protract/retract switch 124 to reverse the polarity of the dry cells 122 across the motor in motor-transmission 154, retracting snare 36 into the distal end 38 of sheath 32.

Movement of thumb control 142 peripherally along the side wall 42 of body 12 is permitted without damage to operating lever 128 of switch 124 by the engagement of lever 128 in the peripherally extending slot 150 of skirt 146. Such peripheral movement of thumb control 142 to the left (counterclockwise about body 12 when viewed from the proximal end 14 thereof) moves operating lever 130 of rotate right/rotate left switch 126 toward the left, coupling the dry cells 122 in a first polarity across the motor of rotate right/rotate left motor-transmission 170, causing rotation of the snare wire 34 toward the left. Movement of the thumb control 142 toward the right (clockwise when viewed from the proximal end 14 of body 12) moves operating lever 130 toward the right, actuating switch 126 to reverse the polarity of cells 122 across the motor in motor-transmission 170, rotating the snare wire 34 and snare loop 36 toward the right. The neutral positions of operating levers 128, 130 disconnect dry cells 122 from both of motor-transmissions 154, 170.

Turning now to the embodiment of the invention illustrated in FIGS. 7–10, those elements numbered identically with the embodiments of FIGS. 1–2 and 5–6 perform the same or similar functions.

The apparatus 10 of FIGS. 7–10 includes a cannula operating handle or body 12 having a proximal end 14, covered by an end cap 16 and a distal end 18. Distal end 18 includes a cap 19 providing an aperture 20 surrounded by a collar 21. Collar 21 extends forward from cap 19 and has outside threads 27 for threadedly engaging a nut 29.

The flared proximal end 30 of a cannula sheath 32 is held in place against collar 21 by tightening nut 29 on threads 27. Sheath 32 is hollow and receives snare wire 34, the diameter of snare wire 34 being sufficiently small that it is freely slidable longitudinally of sheath 32. A snare loop 36 is formed at the distal end 38 of snare wire 34, loop 36 extending beyond the distal end 40 of sheath 32. The particular structure of snare loop 36 can be of any type.

The cannula operating handle 12 includes a generally right circular cylindrical inner wall 42 which slidingly engages the forward and rearward end walls 44, 46, respectively, of a slide 48. Walls 44, 46 are generally circular to the shape to conform to the cross section of inner wall 42 transversely of the longitudinal extent of handle 12. Slide 48 further includes a downwardly opening rack 54. Rack 54 extends the full length of slide 48.

Handle 12 includes a boss 55 providing an opening 56 through the side wall of handle 12. A first thumbwheel 58 is mounted upon an axle 60 for rotation in slot 56. The periphery of thumbwheel 58 is provided with a plurality of teeth 62 to form a pinion gear which engages rack 54. Manipulation of thumbwheel 58 causes slide 48 to slide longitudinally within handle 12.

A spring washer 63 is positioned on axle 60 between adjacent walls 65, 67 (FIG. 9) of boss 55 and thumbwheel 58, respectively, to act as a brake against rotation of thumbwheel 58. The braking force of washer 63 is readily overcome by thumbwheel 58 manipulation but resists accidental longitudinal movement of slide 48. Accidental protraction and retraction of snare loop 36 from its set position relative to the distal end 40 of cannula sheath 32 are thereby avoided.

Forward and rearward end walls 44, 46 are provided with circular cross section aligned apertures 64, 66, respectively. An aperture 68, which is in alignment with apertures 64, 66, is provided in end cap 16. All of apertures 64, 66, 68 are aligned with aperture 20 in end cap 19. A stem 70, which is generally circular in cross section and provided with a chordal, longitudinally extending flat 72, is rotatable in apertures 64, 66, 68. Stem 70 is provided with reduced diameter circular cross section portions 74. C-shaped keeper rings 82 are positioned in the reduced diameter portions 74 of stem 70 to position stem 70 longitudinally with respect to slide 48, while at the same time permitting rotation of stem 70 about its axis within apertures 64, 66. A second thumbwheel 84 having a generally circular aperture 86 with a chordal flat 88 is longitudinally slidably mounted on stem 70. Flat 88 engages flat 72 on the stem, such that rotation of thumbwheel 84 causes rotation of stem 70. Thumbwheel 84 is positioned between walls 44, 46 and is accessible through a slot 90 in the wall 42 of handle 12 for manipulation to rotate stem 70.

A spring washer 91 is positioned on stem 70 between adjacent walls 93, 95 (FIG. 8) of slot 90 and thumbwheel 84, respectively, to act as a brake against rotation of thumbwheel 84. The braking force of washer 91 is readily overcome by thumbwheel 84 manipulation, but resists accidental rotation of stem 70. Accidental rotation of snare loop 36 relative to the distal end 40 of cannula sheath 32 is thereby avoided.

The stem 70 includes a longitudinal passageway 212. Proximal end 94 of snare wire 34 includes a tubular or rod-like metal tip 214 which extends through passageway 212 to near the proximal end 96 of stem 70. Tip 214 is notched at 216 near the proximal end 218 of tip 214. Snare wire 34 and loop 36 are constructed from electrically conductive materials such as woven wire, with the sheath 32 constructed from an insulative material. To make the RF electrical connection to snare wire 34 in this embodiment, a metal sleeve 222 is provided. Sleeve 222 has a longitudinally extending passageway 224 which closely receives tip 214 of the snare wire 34. Sleeve 222 includes a slot 226 adjacent its proximal end 228.

In operation, sleeve 222 is inserted from the proximal end 96 of stem 70 into passageway 212. The slide 48 is adjusted by thumbwheel 58 all the way to the forward end of its travel in handle 12 (toward cap 19). The tip 214 and wire 34 are threaded through passageway 212 past apertures 20, 64, 66, 68. The tip 214 and sleeve 222 are positioned such that notch 216 and slot 226 are aligned and positioned beneath a threaded aperture 230 provided in a boss 232 adjacent the proximal end 96 of stem 70. A screw 234 is then threaded into aperture 230 to a sufficient depth to capture tip 214 and sleeve 222 for longitudinal and rotational movement together with stem 70. The sheath 32 is then drawn toward collar 21 and flared end 30 is captured against collar 21 by nut 29.

A terminal or socket 98 is provided on sleeve 222 for making the necessary electrical connection to an RF generator, not shown. At this time, just prior to plugging the RF generator into socket 98, a cuff 240 can be slid onto the proximal end 14 of handle 12. Socket 98 includes an insulative portion to protect the user from shock by inadvertent contact with sleeve 222 and the conductive portion of socket 98. Cuffs can be provided in different preferred sizes and shapes to accommodate the heel of the operator's hand.

Another advantage of the disclosed systems over systems of the type described in U.S. Pat. No. 3,955,578 is that the RF circuit in the instant systems is enclosed within the body or handle 12 to prevent inadvertent contact with the operator's hands and the like, thereby minimizing the likelihood of RF burns to the operator.

Figure 11:
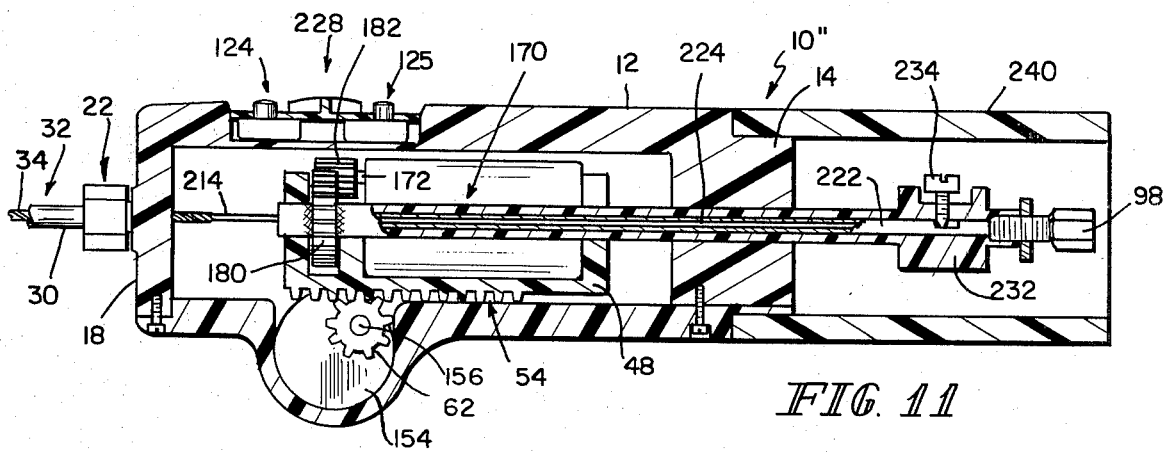
FIG. 11 is a sectional side elevational view of another apparatus constructed according to the present invention.
Figure 12:
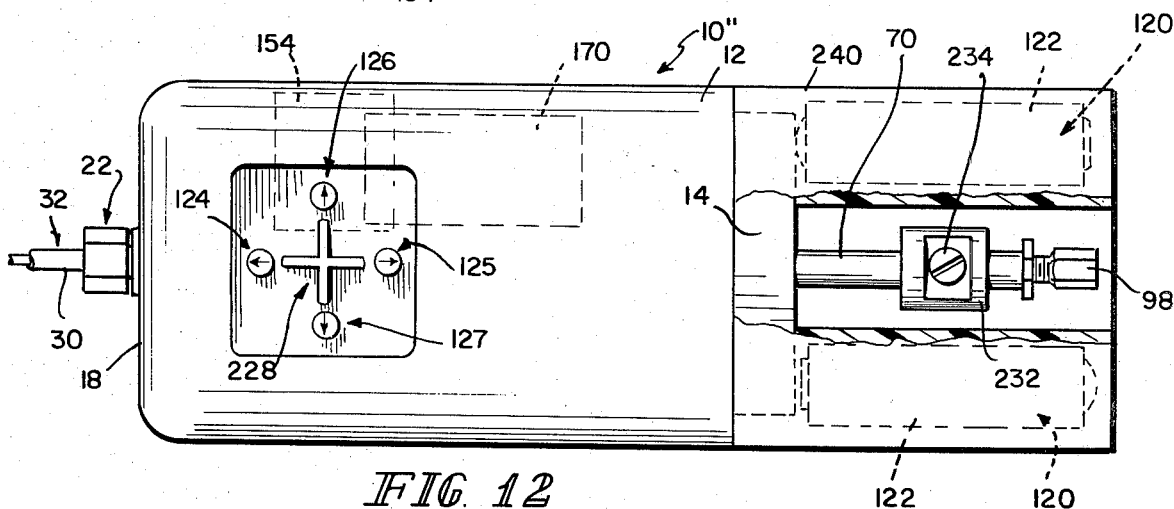
FIG. 12 is a partly sectional top plan view of the apparatus of FIG. 11.
Figure 13:
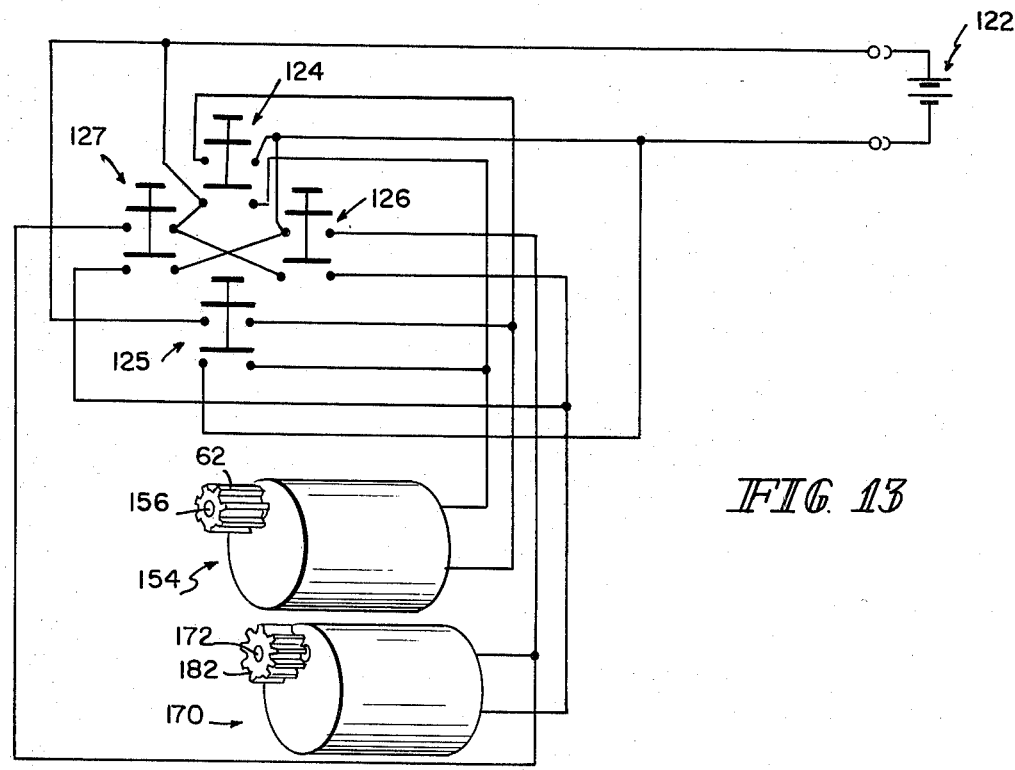
FIG. 13 is a partly block and partly schematic diagram showing the wiring of the electrical system of the embodiment of FIGS. 11-12.

Turning now to the embodiment of the invention illustrated in FIGS. 11-13, those elements numbered identically with the elements in the preceeding embodiments perform the same or similar functions. The apparatus 10" of FIGS. 11-13 includes the cannula operating handle or body 12 having a proximal end 14 and a distal end 18. The proximal end 30 of the cannula sheath 32 is attached to the distal end 18 in the same manner as in the embodiment of FIGS. 1-2, 5-6, and 7-10, i.e., through a threaded aperture, a nut 22 having an aperture, and a collar.

The cannula operating handle 12 includes inner proximal or rearward end portions 120 housing a suitable power source, such as a pair of dry cells 122. Turning to FIG. 13, dry cells 122 are coupled through suitable electrical conductors to a spring-loaded, pushbutton protract electrical switch 124, a spring-loaded pushbutton retract electrical switch 125, a spring-loaded, pushbutton rotate right switch 126 and a spring-loaded pushbutton rotate left switch 127. Switches 124-127 are housed within the cylindrical body 12 at the four points of an index cross section 228 molded into the body 12. Index cross 228 permits the operator to determine which of buttons 124-127 he is about to actuate without requiring him to look at the device 10".

Switches 124 and 125 are coupled by suitable electrical conductors to the terminals of a protract/retract motor-transmission 154 which includes a reversible DC motor. The output shaft 156 of motor-transmission 154 supports a pinion gear 62 engaging a rack 54 provided on a slide 48 mounted for reciprocating movement within body 12. Pushing the button of switch 124 advances the slide 48 toward the distal end 18 of body 12. Pushing the button of switch 125 retracts the entire slide 48 toward the proximal end 14 of body 12.

Rotate right switch 126 and rotate left switch 127 are coupled through suitable conductors to a rotate right-/rotate left motor-transmission 170 which is mounted upon slide 48 for movement therewith. The conductors coupling motor-transmission 170 to switches 126, 127 permit such movement of the motor-transmission 170. The tip 214 at the proximal end 94 of snare wire 34 is coupled to the sleeve 222 through the passageway 212 in stem 70 as in the embodiment of FIGS. 7-10. The stem 70 is also provided with a spur gear 180 which meshes with a spur gear 182 on the motor-transmission 170 output shafts 172. Actuation of the switch 124 protracts the snare 36 from the distal end 38 of sheath 32. Actuation of the switch 125 reverses the polarity of the dry cells 122 across the motor in motor-transmission 154, retracting snare 36 into the distal end 38 of sheath 32. Actuation of switch 126 couples the dry cells 122 in a first polarity across the motor of rotate right/rotate left motor-transmission 170, causing rotation of the snare wire 34 toward the right. Actuation of switch 127 reverses the polarity of cells 122 across the motor in motor-transmission 170, rotating the snare wire 34 and snare loop 36 toward the left.

While a battery 122 power supply is illustrated in the electrically driven embodiments of FIGS. 5, 6, and 11-13, it must be understood that another source, such as a 110 VAC line, could be used to supply power to motors 154, 170.

What is claimed is:

1. An apparatus including a sheath having proximal and distal ends, a member disposed within the sheath and movable longitudinally therein, the movable member having proximal and distal ends, and a surgical instrument operable by movement of the distal end of the movable member with respect to the distal end of the sheath, an operating assembly comprising first means for moving the movable member longitudinally with respect to the sheath, second means for rotating the movable member within the sheath, and a body for supporting the first and second means, the body including a portion for fixed attachment of the proximal end of the sheath thereto, said portion of the body further defining an aperture through which the proximal end of the movable member movably extends, the proximal end of the movable member being coupled to the first and second means for movement thereby, the first means including a slide supported in the body for movement longitudinally thereof, the body including means defining an interior and the slide including means shaped to slide in the interior and a driven portion, the first means further including a first thumbwheel rotatably mounted in the body, the first thumbwheel providing a driving portion to engage the driven portion, the first means further including means for providing a braking force on the first thumbwheel, manipulation of the first thumbwheel overcoming the braking force on the first thumbwheel to cause movement of the slide.

2. The apparatus of claim 1 wherein the second means comprises a stem rotatably mounted with respect to the first means, the stem having proximal and distal ends, the proximal end of the movable member being attached to the stem.

3. The apparatus of claim 2 wherein the stem includes a second thumbwheel for manipulation to rotate the stem with respect to the first means, and means for providing a braking force to the second thumbwheel, manipulation of the second thumbwheel overcoming the braking force on the second thumbwheel to rotate the stem, the second thumbwheel being accessible through the body.

4. The apparatus of claim 3 wherein the proximal end of the stem includes means for providing a terminal for attachment to a source of electrical energy, the stem further including means providing electrical contact between the terminal and the proximal end of the movable member, the movable member also including a conductive portion.

5. For use with a surgical apparatus including a sheath having proximal and distal ends, a member disposed within the sheath and movable longitudinally therein, the movable member having proximal and distal ends, and a surgical instrument operable by movement of the distal end of the movable member with respect to the distal end of the sheath, an operating assembly comprising a body, a slide, the body including means defining an interior and the slide including means shaped to slide within the interior, a stem rotatably mounted on the slide within the body interior, first means controllable from outside the body and engaging the slide and second means controllable from outside the body and engaging the stem, the first and second means being selectively controllable to move the movable member longitudinally of the sheath and to rotate the movable member with respect to the sheath, respectively, the body including means for attachment of the proximal end of the sheath thereto, the body further defining an aperture through which the proximal end of the movable member movably extends, the proximal end of the movable member being coupled to the slide and stem.

6. The apparatus of claim 5 wherein the slide comprises a portion defining a rack and the first rotary means includes a first thumbwheel, the periphery of which provides pinion gear teeth to engage the rack, the first rotary means further including means for applying a braking force to the first thumbwheel, manipulation of the first thumbwheel overcoming the braking force on the first thumbwheel to cause movement of the slide.

7. The apparatus of claim 5 wherein the second rotary means includes a second thumbwheel and means for applying a braking force to the second thumbwheel, manipulation of the second thumbwheel overcoming the braking force on the second thumbwheel to rotate the stem with respect to the slide.

8. The apparatus of claim 5 wherein the proximal end of the stem includes means for retaining a terminal for attachment to a source of electrical energy and a conductor providing electrical contact between the terminal and the proximal end of the movable member, the movable member also being conductive.

9. A surgical apparatus comprising a body providing an interior, a slide slidable within the interior, a stem rotatably mounted on the slide, first means for controlling movement of the slide within the handle, second means for controlling rotation of the stem with respect to the slide, the body including means providing first and second openings, an elongated sheath, a member for movement longitudinally within the sheath, the movable member including an electrically conductive portion, each of the movable member and sheath having a proximal end and a distal end, the proximal end of the sheath being attached to the body and the proximal end of the movable member extending through the first opening, a surgical instrument, and means for mounting the surgical instrument at the distal end of the movable member for protraction, retraction and rotation with respect to the distal end of the sheath in response to movement of the slide and stem, and means for providing electrical power through the conductive portion of the movable member to the surgical instrument, the power-providing means including means providing a first passageway through the stem, a first conductive portion on the movable member proximal end for insertion into the stem passageway from one end, and a second conductive portion for insertion through the second opening into the stem passageway to engage the first conductive portion in conductive engagement.

10. The apparatus of claim 9 wherein the first conductive portion includes an elongated rod-like tip on the proximal end of the movable member for insertion into the distal end of the stem passageway, and the second conductive portion includes an elongated sleeve for insertion into the proximal end of the stem passageway to engage the tip.

11. The apparatus of claim 10 in which the sleeve includes an opening to engage the tip in close-fitting sliding electrical contact.

12. The apparatus of claim 11 wherein the stem includes means providing a second passageway intersecting the first passageway adjacent the proximal end of the stem, the sleeve includes means providing an opening for alignment with the second passageway when the sleeve is inserted fully into the stem first passageway; and further including a pin for insertion into the stem second passageway, through the sleeve opening and into engagement with the tip to fix the sleeve and tip against shifting movement longitudinally of the stem first passageway.

13. The apparatus of claim 12 wherein the tip includes means providing a notch for alignment with the stem second passageway and sleeve opening, the pin for insertion through the sleeve opening and into the tip notch to fix the sleeve and tip.

14. The apparatus of claim 13 wherein the pin and stem second passageway are threaded to prevent unintentional movement of the pin out of engagement with the stem, sleeve and tip.

* * * * *